Feb. 19, 1957 V. B. RODGERS Plant Pat. 1,568
ALMOND TREE
Filed Dec. 10, 1954
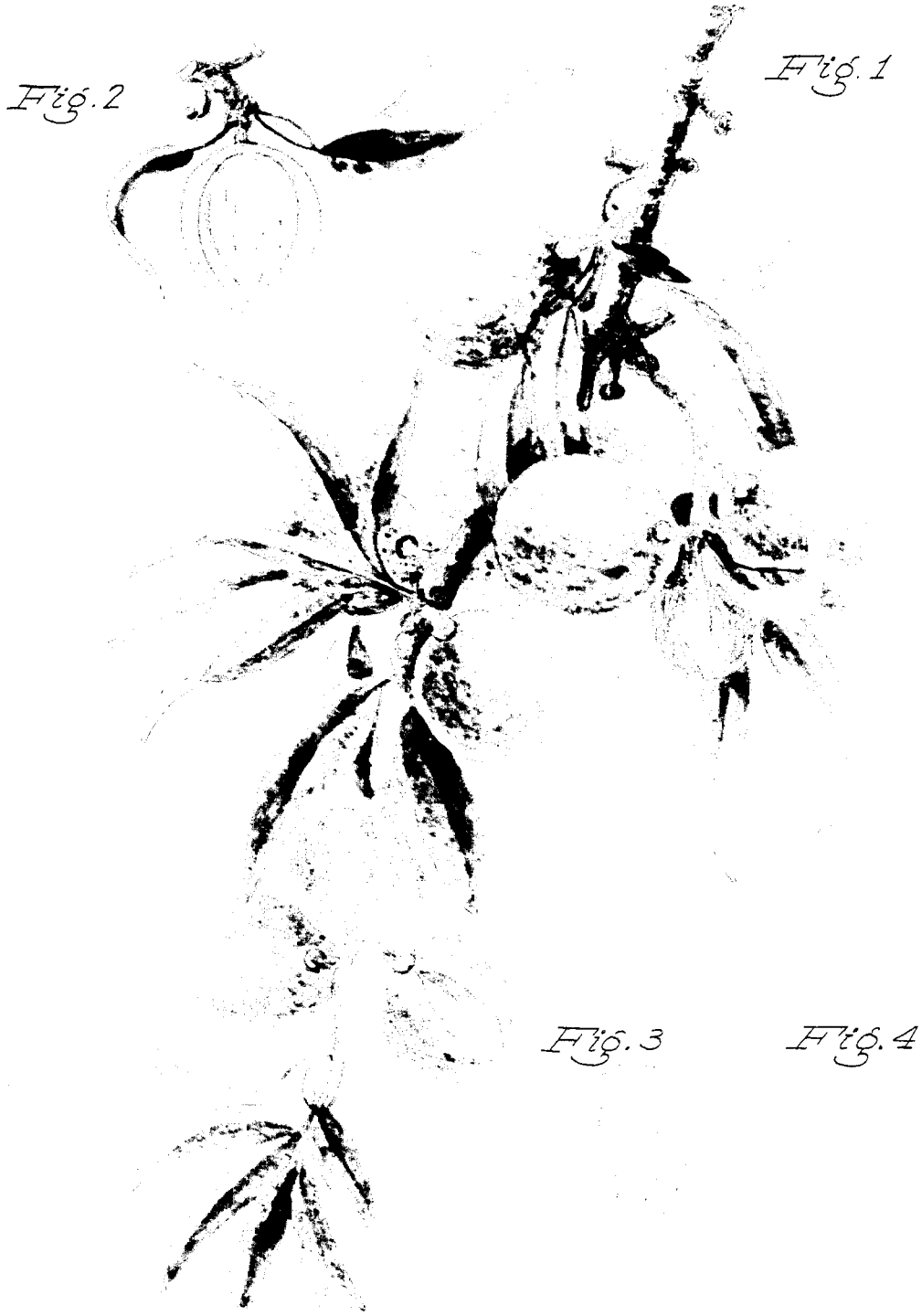
WITNESS
Addison E. Avery
INVENTOR
Vincent B. Rodgers
Webster & Webster
ATTYS.

United States Patent Office

Plant Pat. 1,568
Patented Feb. 19, 1957

1,568

ALMOND TREE

Vincent B. Rodgers, Ballico, Calif.

Application December 10, 1954, Serial No. 474,635
1 Claim. (Cl. 47—62)

This discovery relates to a new and distinct variety of almond tree; the variety having been discoverd by me as a whole tree in an orchard row of otherwise entirely Mission almond nursery trees, June buds on Shalil peach root stock, which I had planted on my ranch near Ballico, Merced County, California. I recognized that the variety was novel by reason of certain distinctive characteristics not only of the three but also of the nut; all of which will hereinafter appear in detail.

Subsequent to its discovery the present variety of almond tree was asexually reproduced, in a nursery at Ceres, Stanislaus County, California, under my direction and control, by budding on seedling root stock; these asexual reproductions having evidenced—at maturity—all of the tree and nut characteristics of the parent.

In comparison to the Mission almond, the present variety bears general resemblance in the tree and fruit, but is distinct therefrom in the following advantageous respects:

As to the tree, it has a considerably greater bearing potential by reason of a faster, more vigorous growing and branching habit, and being considerably broader at the top.

As to the nuts, they are soft shell, and have a substantially higher percentage of crack-out, and a better quality and flavor of the kernel.

The foregoing features of novelty, together with a relatively late blooming period—which makes the variety less susceptible to frost damage—and the fact that the variety serves equally as well as the Mission as a pollinizer, make the variety of especial commercial desirability.

In the original drawings:

Fig. 1 is an elevation of a twig showing leaves and ripe nuts of the variety; certain of the hulls being partially open.

Fig. 2 is an elevation showing one of the nuts with the spur and leaves; the near side of the hull being removed.

Fig. 3 is a somewhat enlarged elevation of one of the nuts as removed from the hull.

Fig. 4 is a somewhat enlarged elevation of one of the kernels as removed from the shell.

Referring now more specifically to the botanical details of this new and distinct variety of almond tree, the following is an outline description thereof; all major color plate identifications being by reference to Maerz and Paul Dictionary of Color:

Tree:

*Density.*—Open.
*Form.*—Vase formed.
*Size.*—Large.
*Vigor.*—Vigorous.
*Branching habit.*—Upright.
*Color of bark.*—Dark brown, almost sooty.
*Foliage.*—Medium.
*Leaves.*—Size—average length, including petiole—101 mm.; average width—23.5 mm. Shape—Lanceolate, bilaterally symmetrical, apex acute, base acute. Margin—crenate; crenations shallow. Color—top side—medium green (21–L–6); bottom side—slightly lighter green (21–H–6).
*Bloom.*—Amount of bloom—heavy. Color—white. Blooming period—averages five days later than Mission almond in period of early bloom; averages the same as the Mission almond in period of late bloom.

Crop:

*Productivity.*—Heavy.
*Disposition of nuts on tree.*—Well distributed.
*Ripening period.*—On or about September 25th; i. e. following the Non-Pareils, but earlier than the Ne Plus-Ultra and Jordanolas.
*Tenacity.*—Tendency to drop early after ripening; easy to harvest; easy to hull.

Hull: Smooth; regular; thin.

*Suture.*—Rigid.
*Color.*—Light green (19–K–2) shading to dark grey (15–A–2).
*Dihiscence.*—Opening freely.
*Splitting.*—Along suture; at sides; freely at base.

Nut:

*Size.*—Average length—28.3 mm.; average width—19.5 mm.; average thickness—14.27 mm.; average weight—2.16 grams.
*Form.* — Length/width — oval. Width/thickness—plump.
*Shell.*—Soft; thin; smooth. Outer shell—crumbling. Inner shell—soft; well sealed. Color—Straw (9–D–3).
*Pits.*—Small; numerous; shallow; round.
*Base.*—ventrally oblique. Stem scar—small; obtuse.
*Apex.*—Obtuse.
*Wing.*—Broad; thin; tapered toward base.
*Inner surface.*—Medium. Ventral streak—dark narrow; long; point acute; corky.
*Percent kernel to nut.*—Average 56%, as compared to 45% from the Mission Almond in the same year and under like growing conditions.

Kernel:

*Size.*—Average length—21 mm.; average width—13 mm.; average thickness—9 mm.; average weight—1.12 grams.
*Form.*—Length/width — Ovate; rounded. Width/thickness—plump.
*Base.*—Ventrally oblique. Stem scar—small.
*Apex.*—Acute; sharp.
*Plumpness.*—Smooth.
*Pellicle.*—Thin.
*Pubescence.*—Smooth.
*Color.*—Light brown (12–J–8) shading to darker brown (14–H–12).
*Number of Doubles.*—None.
*Defective Kernels.*—None.
*Flavor.*—Oily; sweet.
*Quality.*—Very good.

The tree and its nuts herein described may vary in slight detail due to climatic and soil conditions under which the variety may be grown.

As far as I am aware, the hereinbefore mentioned previously existing varieties of almond trees are not patented.

Having thus described my discovery, I claim:

A new and distinct variety of almond tree as shown and described, distinctively characterized—in comparison with the Mission almond, with which there is general resemblance in the three and nuts—by a faster and more vigorous growing and branching habit, the tree having a broader top; and the nuts being soft shell, with a substantially higher percentage of crack-out and a better quality and flavor of the kernel; and further characterized—in comparison to the Soft-Shell Texas almond—by a smooth rather than pubescent kernel.

References Cited in the file of this patent

Department Bulletin 1282, U. S. Department of Agriculture, page 140, plate 15.